United States Patent
Gerstweiler

(10) Patent No.: US 6,571,747 B1
(45) Date of Patent: Jun. 3, 2003

(54) METHOD AND DEVICE FOR PRODUCING ENERGY OR METHANOL

(75) Inventor: Herbert Gerstweiler, Sindelfingen (DE)

(73) Assignees: Michael Prestel, Sindelfingen (DE); Thomas Krebs, Sindelfingen (DE)

( * ) Notice: Subject to any disclaimer, the term of this patent is extended or adjusted under 35 U.S.C. 154(b) by 0 days.

(21) Appl. No.: 09/926,226

(22) PCT Filed: Mar. 22, 2000

(86) PCT No.: PCT/EP00/02517

§ 371 (c)(1),
(2), (4) Date: Sep. 26, 2001

(87) PCT Pub. No.: WO00/58421

PCT Pub. Date: Oct. 5, 2000

(30) Foreign Application Priority Data

Mar. 26, 1999 (DE) .......................................... 199 13 786

(51) Int. Cl.[7] .............................................. F02B 43/08
(52) U.S. Cl. ................................... 123/3; 123/DIG. 12
(58) Field of Search ..................... 123/1 A, 3, DIG. 12

(56) References Cited

U.S. PATENT DOCUMENTS

| | | |
|---|---|---|
| 3,763,205 A | 10/1973 | Green |
| 4,087,449 A | 5/1978 | Marschner et al. |
| 4,372,755 A | 2/1983 | Tolman et al. |
| 4,526,903 A | 7/1985 | Cummings |

FOREIGN PATENT DOCUMENTS

| | | |
|---|---|---|
| DE | 3228532 A1 | 2/1984 |
| DE | 4427322 A1 | 2/1996 |
| DE | 3537527 C2 | 10/1996 |
| DE | 19644684 A1 | 4/1998 |
| DE | 4430750 C2 | 11/1998 |
| DE | 19734259 A1 | 2/1999 |
| DE | 19809400 C1 | 7/1999 |
| EP | 0257018 A2 | 2/1988 |
| EP | 0564796 A1 | 10/1993 |
| EP | 0 699 651 | 2/1994 |
| EP | 0418864 B1 | 4/1994 |
| EP | 0345908 B1 | 11/1994 |
| EP | 0404712 B1 | 7/1995 |
| JP | 2001-152846 A * | 6/2001 |

* cited by examiner

*Primary Examiner*—Noah P. Kamen
(74) *Attorney, Agent, or Firm*—Shlesinger Arkwright & Garvey LLP

(57) ABSTRACT

The invention relates to a method for producing energy, comprising the steps of 1) Burning of fuel in an internal combustion engine thereby producing mechanical energy and a waste gas containing carbon dioxide and water vapor, 2) Reducing the carbon dioxide and water vapour waste gas components in an environment containing organic material into a synthesis gas which contains carbon dioxide and hydrogen, and 3) Feeding the synthesis gas produced in step 2 to the internal combustion engine. To produce methanol, a methanol synthesis is introduced between steps 2 and 3 of the method set forth above.

15 Claims, 1 Drawing Sheet

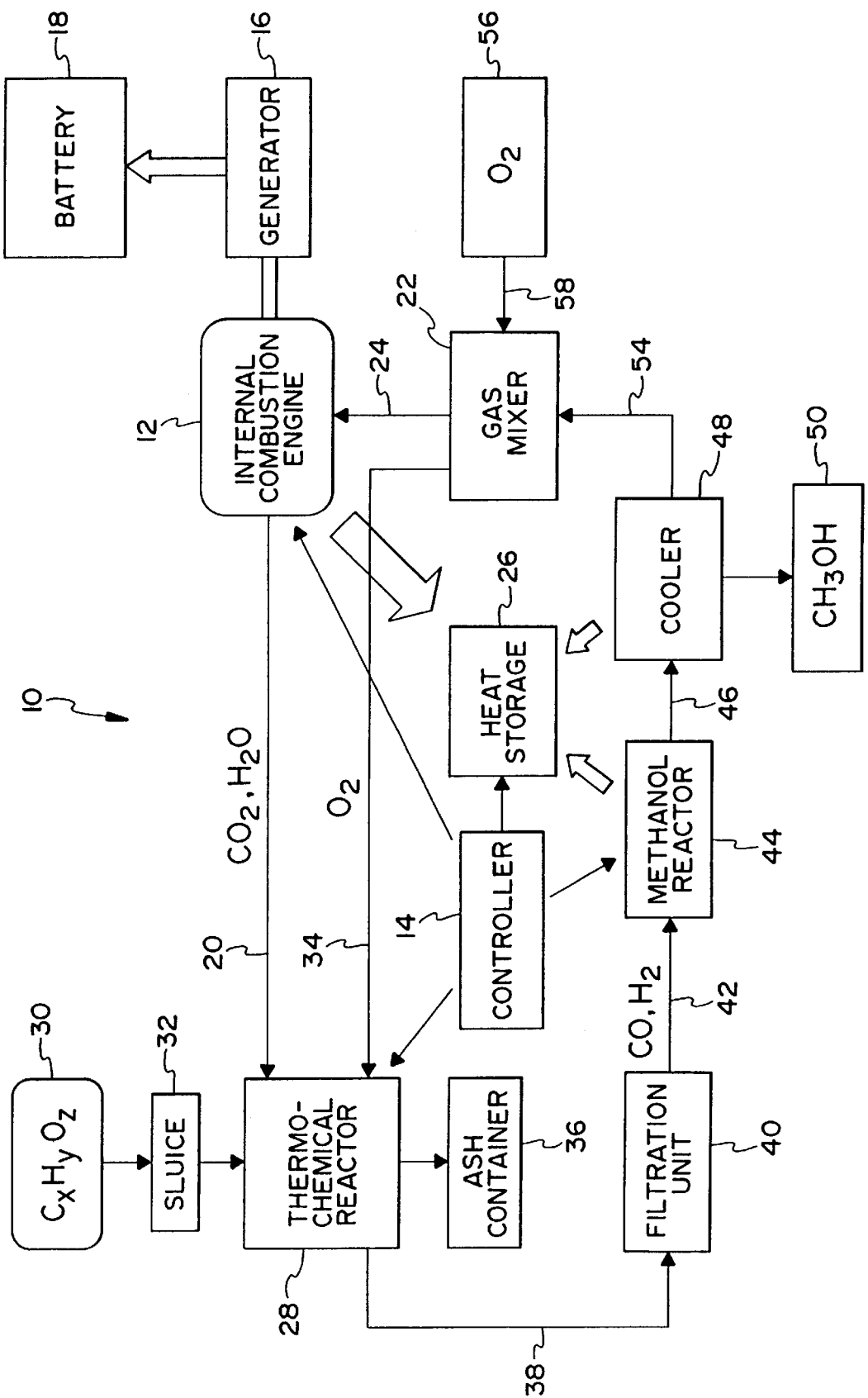

METHOD AND DEVICE FOR PRODUCING ENERGY OR METHANOL

The present invention relates to a process and an apparatus for the production of energy and a process and an apparatus for the production of methanol.

Numerous processes and apparatus are already known for the production of energy and/or methanol from organic raw materials.

Some of these processes and apparatus are based on the principle that an organic material is subjected to controlled oxidation wherein the energy carrier hydrogen is produced. The obtained hydrogen is supplied to a fuel cell and converted into current, according to the actual current requirements. Since storage of excess gaseous hydrogen is laborious and must especially satisfy stringent safety requirements when used in private households, hydrogen is normally catalytically converted together with carbon monoxide or carbon dioxide into the fluid energy carrier methanol in order to store its energy content, wherein the hydrogen can be re-extracted from the methanol and converted into current according to requirements by means of a reforming reaction.

A process for the storage of energy present in the form of hydrogen is disclosed in DE 196 44 684 A1, wherein carbon dioxide, especially resulting from exhaust emissions, is converted after mixing with the hydrogen in a reactor into the energy carriers methane, methanol or ethanol.

A process and an apparatus for the production of electrical energy from bio-raw materials is disclosed in DE 44 30 750 C2, wherein a hydrogen and carbon monoxide-containing crude fuel gas is produced from the bio-raw materials by means of partial oxidation with an oxygen-containing gasification medium in an oxidation reactor. From the fuel gas, the hydrogen proportion is placed into intermediate storage by reaction with a storage material, especially a so-called hydride store or with metal oxides, so that rapid removal of the hydrogen from the storage can be carried out according to requirements, and the hydrogen can be transported into a fuel cell module for conversion into current.

A process and an apparatus for the production of hydrogen by means of the gasification of bio-raw materials is disclosed in DE 197 34 259 A1, wherein the bio-raw material is gasified into a hydrogen-containing crude gas in the presence of supplied water vapour in a vaporization reactor. The hydrogen proportion of the crude gas is separated from the residual gas at especially-high purity and can either be converted into current in a fuel cell, stored as methanol by synthesis with carbon dioxide or used for other purposes. In order to increase the degree of effectiveness in this process, the energy content of the low-hydrogen residual gas is also used in that it is combusted either in a closed cycle for the production of heat energy for the creation of water vapour or outside the cycle.

A process is known from EP 0 257 018 A2 for thermal utilisation of waste and/or waste fuels, wherein the waste and/or waste fuels are supplied to a gasifying reactor which is directly heated with gas and/or oil and the gases extracted from the gasifying reactor are supplied to a combustion chamber for the production of energy, especially for the production of steam. A portion of the flue gases from the combustion chamber is fed back to the gasifying reactor under pressure.

A process is known from DE 32 28 532 A1 for the carbonisation and gasification of solids which contain carbon wherein hot gases, amongst others, are used to heat the reactors, these gases being produced in a combustion chamber by combustion of a portion of the carbonisation gas produced in the carbonisation zone.

In "Energy Recovery From Waste: The Application of Gasification Technologies", La Chimica e l'Industria, 1996, No. 5, pp. 603–607, P. Pollesel gives an overview of the use of gasification processes to extract energy from waste, especially from bio-mass. Amongst other things, Pollesel mentions that the gases produced during gasification can be combusted in a gas turbine or a diesel engine to produce mechanical energy which can then be converted into electrical energy.

Consequently, the object of the present invention is to provide a process and an apparatus for the production of energy and methanol respectively wherein optimised exploitation of the energy content of the organic starting material occurs in order to attain especially economical operation, and simultaneously allowing control of the proportions of released and stored energy respectively, according to requirements.

A process according to claim 1 and an apparatus according to claim 9 or 11 is suggested as a solution for this object. The process for the production of energy, according to the invention, comprises the following steps:

1. Combustion of fuel in an internal combustion engine to create mechanical energy and hot exhaust gas which contains carbon dioxide and water vapour,
2. Reduction of the hot exhaust gas components carbon dioxide and water into a synthesis gas which contains carbon monoxide and hydrogen in an environment containing a supplied organic material,
3. Supply of the synthesis gas produced in step 2 to the internal combustion engine.

According to claim 7, methanol synthesis is inserted between steps 2 and 3 of the process according to the invention in order to produce methanol.

The steps of the process, according to the invention are set out for a recirculating operation, from which at different points energy in the form of electrical energy (current), heat energy and stored chemical energy (methanol) can be removed and/or added at various points, wherein the removal and supply can be regulated according to requirements, allowing optimised utilisation of the energy content of the organic starting material.

Therefore in accordance with the invention, a fuel which is preferably fluid or gaseous and contains hydrocarbon is combusted on supply of air or oxygen in an internal combustion engine, creating mechanical energy, exhaust gas and heat energy. The exhaust gas released by the internal combustion engine, which contains carbon dioxide and water vapour, is supplied to a thermochemical reactor in which organic material such as biomass, coal, organic waste and such like is present. In the thermo-chemical reactor, carbon dioxide and water are reduced into carbon monoxide and hydrogen from the exhaust gas stream from the internal combustion engine, whilst the organic material is oxidised. The temperature required for the reaction is produced by the heat energy of the exhaust gas stream. Insofar as the temperature attainable by the inflowing exhaust gas is not sufficient to start or to maintain the reaction, a part of the hot exhaust gas stream from the internal combustion engine can be separated from the rest of the stream and used as an external heat supply for heating the thermochemical reactor and/or the temperature level required for the reaction can be increased by the supply of oxygen or air. Advantageously, the temperature of the hot exhaust gas is between approximately 900° C. and approximately 1000° C. In this way, the hot exhaust gas from the internal combustion engine is directly used as a valuable energy carrier whilst the mechanical energy produced by the internal combustion engine is available for other purposes.

A synthesis gas which contains carbon monoxide and hydrogen is produced in the thermo-chemical reactor under suitable pressure and temperature conditions. The synthesis gas may contain other non-troublesome components such as, for example, carbon dioxide or methane, and undesired or troublesome solid, fluid and/or gaseous components such as, for example, suspended particles or sulphurous gases. The troublesome or undesired components can have a disadvantageous effect on further steps of the process, according to the invention, e.g. they can cause deactivation of a catalyst. Hence a filtration step is provided downstream for removal of the undesired or troublesome components.

The synthesis gas from the thermo-chemical reactor which contains carbon monoxide and hydrogen and which has been purified in the filtration step is mixed in a gas mixing unit with air oxygen or oxygen from an oxygen tank and is supplied to the internal combustion engine as a fuel. In this way, the supply of the thermo-chemical redox process with hot exhaust gas is ensured.

Insofar as more synthesis gas is produced than is required for the operation of the internal combustion engine, as an alternative the synthesis gas, which contains carbon monoxide and hydrogen and which has been purified in the filtration process can be synthesised into the energy carrier methanol from carbon monoxide and hydrogen or carbon dioxide and hydrogen in an exothermic reaction according to a conventional process in a reactor which contains a suitable catalyst. Apart from heat energy, resultant reaction products are methanol and optionally water as well as non-converted synthesis gas. The reaction products are cooled in a downstream cooling unit. The precipitating methanol can be fed into a tank and stored. According to requirements, the stored methanol can be supplied to the internal combustion engine as a fuel, or used for other purposes e.g. as a fuel for motor vehicles.

Excess, non-converted residual synthesis gas from the methanol synthesis is supplied to the internal combustion engine as described above.

In an embodiment of the Invention, the mechanical energy produced by the internal combustion engine is transformed into current by means of a generator. The current can either be available for the supply of a private household, stored in batteries or fed into the supply mains.

In a further embodiment of the invention, a fuel cell in a fuel cell unit is supplied via a gas mixer with oxygen and hydrogen in order to produce current, wherein the oxygen can be supplied from an oxygen tank or can be air oxygen and the hydrogen either originates from the synthesis gas purified by the filtration process or by reformation from the stored methanol. An especially-high degree of effectiveness for conversion of stored chemical energy into electrical energy can be attained with this type of current production. Furthermore, it is possible to adapt the production of current to an existing load by using the chemical energy of the stored methanol.

In an especially advantageous embodiment of the invention, heat resulting from the individual process steps, especially the radiated heat of the internal combustion engine, the generator, the methanol reactor and the cooling unit, can be supplied to a heat store where it is available, for example, for heating the thermo-chemical reactor or for heating rooms.

In a further especially advantageous embodiment of the invention, the material and energy streams can be controlled by means of a controller, e.g. a microprocessor control. This especially relates to the control of exhaust gas supply from the internal combustion engine into the thermo-chemical reactor, the control of the gas streams in the gas mixing unit, the monitoring and control of the parameters of the methanol synthesis, temperature regulation in various process steps, regulation of the energy streams of the heat storage and monitoring the level or regulation of the supply of organic material into the thermo-chemical reactor. In this way, optimum supply of the elements of the individual process steps with substrates and energy is attained at all times. Simultaneously, the energy content of the fuel is optimally used and adaptation of energy extraction and energy storage to the respective requirements is made possible.

In order to further solve the object which forms the basis of the invention, an apparatus is suggested for the production of energy and/or methanol, especially for implementation of the hereinbefore-described process. The apparatus, according to the invention, comprises an internal combustion engine, a thermo-chemical reactor disposed downstream of the internal combustion engine for reduction of the exhaust gas, which is produced in the internal combustion engine and which contains carbon dioxide and water steam, into a synthesis gas which contains carbon monoxide and hydrogen. An inlet is provided for the synthesis gas into the internal combustion engine so that energy may be produced. For the production of methanol, a methanol reactor is disposed downstream of the thermo-chemical reactor for Synthesis of methanol from the synthesis gas of the thermo-chemical reactor, wherein the synthesised residual gas and/or methanol from the methanol synthesis are fed into the internal combustion engine.

In an advantageous embodiment of the invention, a generator which can be driven by the internal combustion engine is provided for the production of current. Furthermore, a fuel cell apparatus disposed downstream of the thermo-chemical reactor can be provided for the production of current from methanol and/or at least part of the hydrogen produced in the thermo-chemical reactor.

In a further embodiment of the apparatus according to the invention, in order to store energy a heat storage is provided for storage of the heat generated with the apparatus. The heat storage serves especially for storage of the radiated heat from the exothermic process steps, for example from the internal combustion engine, the generator, the methanol synthesis and/or the cooling unit. The stored radiated heat is used in the exothermic process steps in the thermo-chemical reactor or for other purposes. Furthermore, a methanol tank is provided for storage of the synthesised methanol, wherein the stored methanol can be supplied to the internal combustion engine and/or the fuel cell apparatus if required.

Other advantages and embodiments of the invention can be seen in the description and the accompanying drawing.

The Invention is schematically represented in the drawing with reference to an embodiment example, and is described in detail in the following text with reference to the drawing.

The single FIGURE shows, in a strongly-schematic block diagram, an apparatus according to the Invention, for the production of energy and methanol.

The FIGURE shows an apparatus 10 according to the invention, for the production of energy and methanol with an internal combustion engine 12 which combusts a fuel which contains hydrocarbon to create mechanical energy, hot exhaust gas and radiated heat. The generated mechanical energy is transformed into current by means of a generator 16, this current being either stored in a battery 18 or fed directly into the supply mains, or being used directly, for example in a private household. The radiated heat of the internal combustion engine 12 and the radiated heat of the generator 16 are supplied to a heat store 26. The internal combustion engine 12 is supplied with the gaseous fuel and oxygen by means of a fuel gas line 24 from a gas mixer 22.

The exhaust gas given off by the internal combustion engine contains carbon dioxide and water and should advantageously have a temperature of approximately 900° C. to approximately 1000° C. The hot exhaust gas is fed into a thermo-chemical reactor 28 via an exhaust gas pipe 20. Organic material is filled into the thermo-chemical reactor 28 from a storage container 30 via a sluice 32. The level of the container 30 and the quantity of organic material which is to be filled via the sluice 32 can preferably be controlled via a controller 14.

The organic material which is fed into the thermo-chemical reactor 28 is heated by the hot stream of exhaust gas from the internal combustion engine 12 to approximately 900° C. to approximately 1000° C. If the heat quantity provided by the exhaust gas stream is insufficient to attain the required temperature, a portion of the hot exhaust gas stream is separated off and is used to heat the thermo-chemical reactor 28. In addition, stored heat energy from the heat store 26 can be used. Furthermore, it is possible to increase the temperature by supplying oxygen or air from the gas mixer 22 into the thermo-chemical reactor 28 via a first oxygen pipe 34. In the thermo-chemical reactor 28, carbon dioxide and water are reduced to a synthesis gas with the named temperature conditions, whilst the organic material is oxidised.

The synthesis gas is removed from the thermo-chemical reactor by means of a synthesis gas pipe 38. Under the temperature and pressure conditions which are to be set in the thermo-chemical reactor 28, the synthesis gas contains mainly hydrogen and carbon monoxide. Carbon dioxide, methane, water and suspended particles can also occur as accessory components of the expelled synthesise gas.

Ash also occurs as the further product of the redox reaction which occurs in the thermo-chemical reactor 28, this ash mainly comprising mineral components of the original organic material which are not completely oxidised. The ash is collected in a ash container 36. The level of the ash container 36 and its emptying are preferably monitored and controlled by the controller 14.

The synthesis gas produced in the thermo-chemical reactor 28 is supplied to a filtration unit 40 via the synthesis gas pipe 38. In the filtration unit 40, the synthesis gas is first freed from solid and fluid suspended particles, and preferably also other minor components which e.g. contain sulphur and would prove troublesome in the subsequent catalytic steps. The pure synthesis gas which was purified in the filtration unit 40, and which primarily contains hydrogen and carbon monoxide, can either be directly fed into the gas mixer unit 22 and from there supplied to the internal combustion engine 12 as a fuel via the combustion gas pipe 24, or can be supplied to a methanol reactor 44. A catalyst which is suitable for methanol synthesis is provided in the methanol reactor 44. Depending an the composition of the pure synthesis gas, the following reactions can occur:

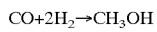

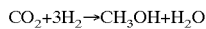

As products of the methanol synthesis, methanol and non-converted components of the pure synthesis gas are fed into a cooler 48 via a first pure gas pipe 46. Methanol and optionally water precipitate in the cooler 48, whilst the remaining gas is supplied to the gas mixer 22 via a second pure gas pipe 54, is there mixed with oxygen or air and can then be supplied to the internal combustion engine 12 as a fuel via the combustion gas pipe 24. The methanol which precipitates in the cooler 48 can be transferred via a methanol pipe 52 to a methanol tank 50, where it can be stored. The stored methanol is then available when required as a fuel for the internal combustion engine 12, or can be used for other purposes, e.g. as a fuel for motor vehicles. The radiated heat from the methanol reactor 44 and the cooler 48 are advantageously transferred to the heat storage 26 where they are stored.

The gas supply and mixing in the gas mixer 22 can also advantageously be controlled via the control unit 14. Here, the gas mixer 22 obtains, via a second oxygen pipe 58, oxygen from an oxygen tank 56 or air which is necessary for supplying the thermo-chemical reactor 28 and the internal combustion engine 12, and gaseous fuel, optionally placing a part of the gaseous fuel into intermediate storage as methanol, via the second pure gas pipe 54 for supplying the internal combustion engine 12.

Hence current, heat and the energy carrier methanol are produced with the invention to a high degree of effectiveness from cheaply-sourced organic material. The arrangement of the apparatus as a cyclical system allows control of the material and energy streams according to requirements. Even when no organic material is available, the apparatus according to the invention can fundamentally be operated at any time with methanol produced within the frame of the process or with other external fuels to ensure energy production. The process and the apparatus, according to the invention, are thus especially suitable for use in private households if extensively self-sufficient energy production is desired. With regard to the production of regenerative energy, the process, according to the invention, can also be used in increased scales as an alternative to block heating power stations.

What is claimed is:

1. A process for the production of energy with the following steps:
    1. combustion of fuel in an internal combustion engine to create mechanical energy and hot exhaust gas which contains carbon dioxide and water vapour,
    2. reduction of the hot exhaust gas components carbon dioxide and water into a synthesis gas which contains carbon monoxide and hydrogen in an environment containing a supplied organic material,
    3. supply of the synthesis gas produced in step 2 to the internal combustion engine.

2. A process according to claim 1, wherein in step 1 the mechanical energy is converted into current by means of a generator.

3. A process according to claim 1 wherein the environment which contains the supplied organic material is a thermo-chemical reactor with bio-mass, coal or organic waste supplied to it.

4. A process according to claim 1 and wherein at least part of the hydrogen produced in step 2 is supplied to a fuel cell apparatus for the production of current.

5. A process according to claim 1 and wherein heat occurring in the individual process steps is supplied to a heat store.

6. A process according to claim 1 and wherein a portion of the exhaust gas produced in step 1 is used to heat the environment which contains the organic material.

7. A process according to claim 1 and wherein methanol is synthesised and separated out from the synthesis gas resulting from the reduction in step 2 and in step 3 non-converted residual synthesis gas and/or synthesis methanol is optionally supplied to the internal combustion engine.

8. A process according to claim 7, wherein synthesised methanol is supplied to a methanol tank or a fuel cell apparatus.

9. An apparatus for the generation of energy comprising an internal combustion engine, said internal combustion engine producing a hot exhaust gas containing carbon dioxide and water vapour, a thermo-chemical reactor disposed downstream of said internal combustion engine, said thermo-chemical reactor adapted to receive a supplied organic material and reduce the hot exhaust gas into a synthesis gas which contains carbon monoxide and hydrogen and, means for supplying the synthesis gas to said internal combustion engine.

10. An apparatus according to claim 9, wherein downstream of said thermo-chemical reactor, a fuel cell apparatus is provided to generate current from at least part of the hydrogen produced in said thermo-chemical reactor.

11. An apparatus according to claim 9 and further including a generator adapted to be driven by said internal combustion engine to generate a current.

12. An apparatus according to claim 9 and further including a heat store for storing the heat generated by said apparatus.

13. An apparatus for the production of energy and methanol comprising an internal combustion engine, said internal combustion engine producing a hot exhaust gas containing carbon dioxide and water vapour, a thermo-chemical reactor disposed downstream of said internal combustion engine, said thermo-chemical reactor adapted to receive a supplied organic material and reduce the hot exhaust gas into synthesis gas which contains carbon monoxide and hydrogen, a methanol reactor disposed downstream of said thermo-chemical reactor for synthesis of methanol from the synthesis gas of said thermo-chemical reactor and, means for supplying at least one of residual synthesis gas and methanol to said internal combustion engine.

14. An apparatus according to claim 13 and further including a methanol tank for storage of the synthesised methanol.

15. An apparatus according to claim 13, and further including a fuel cell apparatus for the production of current from methanol.

* * * * *